(12) United States Patent
Yang

(10) Patent No.: US 6,379,382 B1
(45) Date of Patent: Apr. 30, 2002

(54) STENT HAVING COVER WITH DRUG DELIVERY CAPABILITY

(76) Inventor: Jun Yang, 46 Foxtail La., Dove Canyon, CA (US) 92679

( * ) Notice: Subject to any disclaimer, the term of this patent is extended or adjusted under 35 U.S.C. 154(b) by 0 days.

(21) Appl. No.: 09/524,650

(22) Filed: Mar. 13, 2000

(51) Int. Cl.⁷ .................................................. A61F 2/06
(52) U.S. Cl. ..................................... 623/1.42; 623/1.13
(58) Field of Search ............................... 623/1.39–1.48

(56) References Cited

U.S. PATENT DOCUMENTS

| | | |
|---|---|---|
| 3,657,744 A | 4/1972 | Ersek |
| 3,988,782 A | 11/1976 | Dardik et al. |
| 4,140,126 A | 2/1979 | Choudhury |
| 4,925,710 A | 5/1990 | Buck et al. |
| 5,122,154 A | 6/1992 | Rhodes |
| 5,123,917 A | 6/1992 | Lee |
| 5,286,254 A | 2/1994 | Shapland et al. |
| 5,383,928 A * | 1/1995 | Scott et al. ............. 623/1.42 |
| 5,389,106 A | 2/1995 | Tower |
| 5,411,550 A | 5/1995 | Herweck et al. |
| 5,466,509 A | 11/1995 | Kowligi et al. |
| 5,507,771 A | 4/1996 | Gianturco |
| 5,562,697 A | 10/1996 | Christiansen |
| 5,562,728 A | 10/1996 | Lazarus et al. |
| 5,578,075 A * | 11/1996 | Dayton ...................... 623/1.42 |
| 5,584,877 A | 12/1996 | Miyake et al. |
| 5,609,629 A | 3/1997 | Fearnot et al. |
| 5,616,608 A | 4/1997 | Kinsella et al. |

(List continued on next page.)

FOREIGN PATENT DOCUMENTS

| | | |
|---|---|---|
| EP | 0646365 | 4/1995 |
| EP | 0657147 | 6/1995 |
| EP | 0667132 | 8/1995 |
| EP | 0714269 | 6/2000 |
| WO | 9501761 | 1/1995 |
| WO | 9509586 | 4/1995 |
| WO | WO 95/10989 | 4/1995 |
| WO | 9607371 | 3/1996 |
| WO | WO 97/24081 | 7/1997 |
| WO | WO 98/25545 | 6/1998 |
| WO | 9825546 | 6/1998 |
| WO | WO 98/31305 | 7/1998 |
| WO | WO 98/34669 | 8/1998 |
| WO | WO 98/56312 | 12/1998 |
| WO | WO 99/15104 | 4/1999 |
| WO | WO 99/27989 | 6/1999 |
| WO | WO 99/38455 | 8/1999 |
| WO | WO 00/09041 | 2/2000 |
| WO | WO 00/12147 | 3/2000 |
| WO | WO 01/15633 | 3/2000 |
| WO | WO 00/18328 | 4/2000 |

(List continued on next page.)

Primary Examiner—David H. Willse
Assistant Examiner—Suzette J. Jackson
(74) Attorney, Agent, or Firm—Raymond Sun

(57) ABSTRACT

A prosthesis has a cylindrical stent, and a cover provided about the outer periphery of the stent. The cover has at least two layers of materials, with at least one layer of material being permeable to drugs. The layers of material can define at least one chamber therebetween, with a drug loaded into the at least one chamber. Alternatively, the drug can be loaded into the material of one or more layers.

39 Claims, 3 Drawing Sheets

U.S. PATENT DOCUMENTS

| | | |
|---|---|---|
| 5,620,763 A | 4/1997 | House et al. |
| 5,628,784 A | 5/1997 | Strecker |
| 5,628,788 A | 5/1997 | Pinchuk |
| 5,637,113 A | 6/1997 | Tartaglia et al. |
| 5,674,241 A | 10/1997 | Bley et al. |
| 5,693,085 A * | 12/1997 | Buirge et al. ............... 623/1.47 |
| 5,697,967 A * | 12/1997 | Dinh et al. ................ 623/1.42 |
| 5,700,285 A | 12/1997 | Myers et al. |
| 5,700,286 A | 12/1997 | Tartaglia et al. |
| 5,707,385 A | 1/1998 | Williams |
| 5,709,874 A | 1/1998 | Hanson et al. |
| 5,718,973 A | 2/1998 | Lewis et al. |
| 5,723,004 A | 3/1998 | Dereume et al. |
| 5,725,567 A | 3/1998 | Wolff et al. |
| 5,735,892 A | 4/1998 | Myers et al. |
| 5,735,897 A | 4/1998 | Buirge |
| 5,769,883 A | 6/1998 | Buscemi et al. |
| 5,779,732 A | 7/1998 | Amundson |
| 5,788,626 A * | 8/1998 | Thompson ................... 600/36 |
| 5,843,166 A | 12/1998 | Lentz et al. |
| 5,857,998 A | 1/1999 | Barry |
| 5,865,723 A | 2/1999 | Love |
| 5,873,904 A | 2/1999 | Ragheb et al. |
| 5,876,432 A | 3/1999 | Lau et al. |
| 5,897,589 A | 4/1999 | Cottenceau et al. |
| 5,902,332 A | 5/1999 | Schatz |
| 5,925,074 A | 7/1999 | Gingras et al. |
| 5,925,075 A | 7/1999 | Myers et al. |
| 5,941,895 A * | 8/1999 | Myler et al. ................ 606/195 |
| 5,948,018 A | 9/1999 | Dereume et al. |
| 5,951,586 A | 9/1999 | Berg et al. |
| 5,957,974 A | 9/1999 | Thompson et al. |
| 5,961,545 A | 10/1999 | Lentz et al. |
| 5,968,070 A | 10/1999 | Bley et al. |
| 5,980,565 A | 11/1999 | Jayaraman |
| 5,990,379 A | 11/1999 | Gregory |
| 6,013,099 A | 1/2000 | Dinh et al. |
| 6,117,166 A | 9/2000 | Winston et al. |
| 6,156,064 A * | 12/2000 | Chouinard ................ 623/1.44 |
| 6,187,039 B1 * | 2/2001 | Hiles et al. ................ 623/1.44 |
| 6,193,746 B1 * | 2/2001 | Strecker .................... 623/1.13 |
| 6,206,915 B1 * | 3/2001 | Fagan et al. ............... 623/1.42 |
| 6,124,039 A1 | 4/2001 | Banas et al. |
| 6,218,016 B1 | 4/2001 | Tedeschi et al. |
| 6,248,122 B1 | 6/2001 | Klumb et al. |
| 6,254,627 B1 | 7/2001 | Freidberg |

FOREIGN PATENT DOCUMENTS

| | | |
|---|---|---|
| WO | WO 00/33768 | 6/2000 |
| WO | WO 00/42949 | 7/2000 |
| WO | WO 00/48530 | 8/2000 |
| WO | WO 00/49973 | 8/2000 |
| WO | WO 00/50116 | 8/2000 |
| WO | WO 01/26707 | 4/2001 |

* cited by examiner

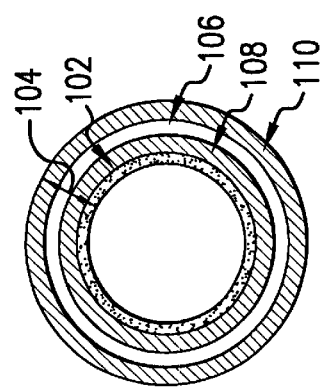
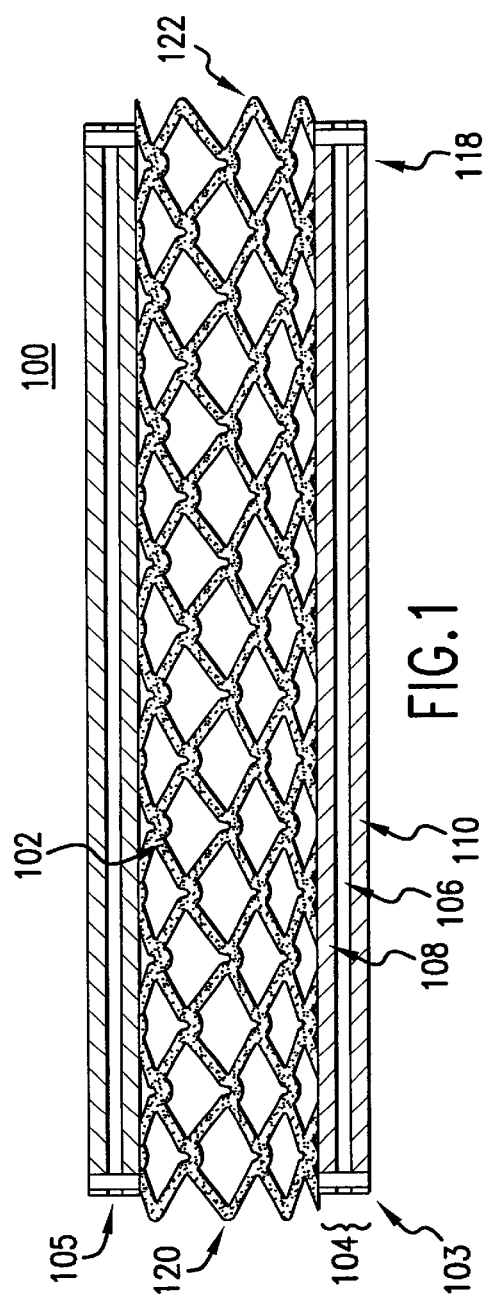

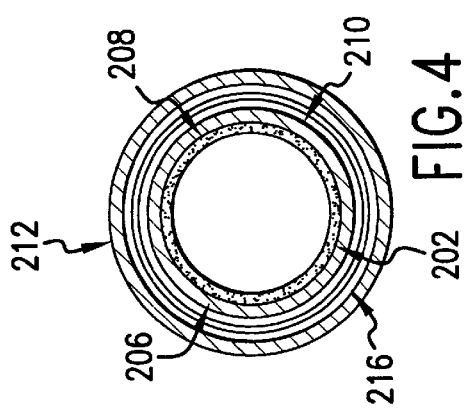
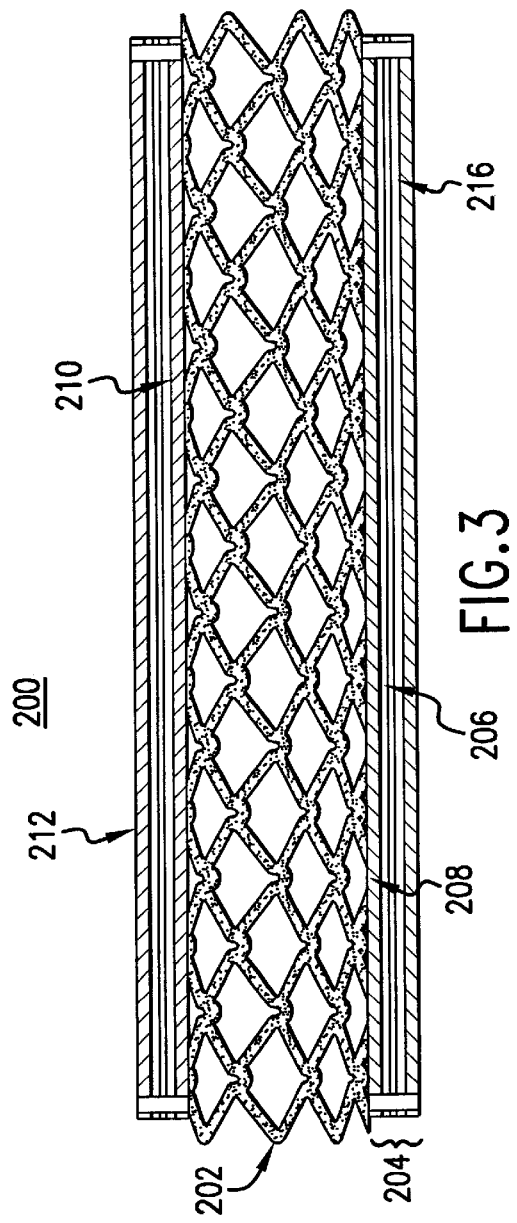

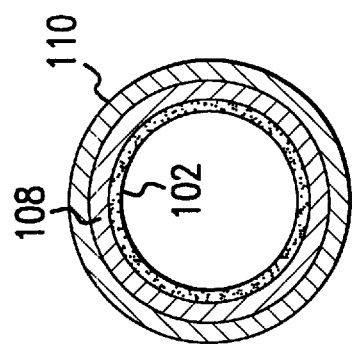
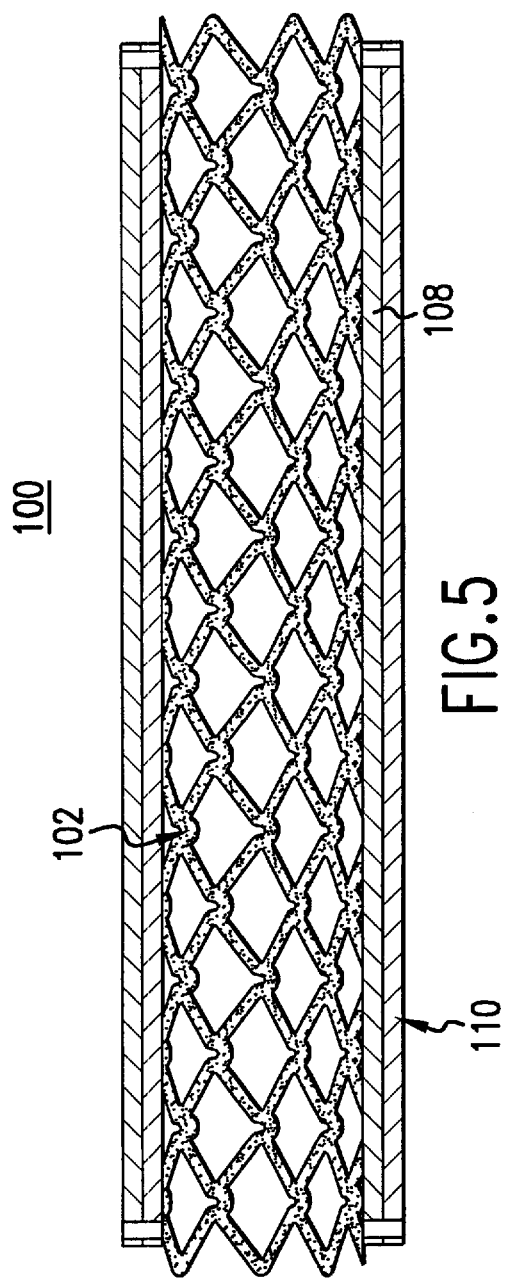

STENT HAVING COVER WITH DRUG DELIVERY CAPABILITY

BACKGROUND OF THE INVENTION

1. Field of the Invention

The present invention relates to prostheses for implantation into a mammalian vessel, and in particular, to intraluminal stents that are provided with a cover that can deliver and release drugs.

2. Description of the Prior Art

The treatment of stenosis is the subject of much research and discussion. Stenosis are currently being treated by a number of well-known procedures, including balloon dilatation, stenting, ablation, atherectomy or laser treatment.

Restenosis is the renarrowing of a peripheral or coronary artery after trauma to that artery caused by efforts to open a stenosed portion of the artery, such as by balloon dilatation, ablation, atherectomy or laser treatment of the artery. For such procedures, restenosis occurs at a rate of about 20–50% depending on the definition, vessel location, lesion length and a number of other morphological and clinical variables. Restenosis is believed to be a natural healing reaction to the injury of the arterial wall that is caused by angioplasty procedures. The host reaction begins with the thrombotic mechanism at the site of the injury. The final result of the complex steps of the healing process can be intimal hyperplasia, the uncontrolled migration and proliferation of medial smooth muscle cells, combined with their extracellular matrix production, until the artery is again stenosed or occluded.

Many attempts have been made or suggested to treat stenosis, and to prevent or minimize restenosis. One common approach is to implant intravascular stents in coronary and peripheral vessels. The stent is usually inserted by a delivery system (e.g., such as a catheter) into a vascular lumen and expanded (either via a balloon on a catheter, or through self-expansion) into contact with the diseased portion of the arterial wall to provide mechanical support for the lumen. The positioning of stent in the lumen can be used to treat stenosis by re-opening the lumen that had been partially blocked by the stenosis. However, it has been found that restenosis can still occur with such stents in place. In addition, a stent itself can cause undesirable local thrombosis. To address the problem of thrombosis, persons receiving stents also receive extensive systemic treatment with anti-coagulant and antiplatelet drugs.

To address the restenosis problem, a number of approaches have been suggested. One type of approach relates to the delivery of drugs to minimize restenosis. As one example, these drugs can be delivered via oral, intra-vascular or intramuscular introduction, but these attempts have been largely unsuccessful. Unfortunately, pills and injections are known to be ineffective modes of administration because constant drug delivery and higher local concentration are very difficult to achieve via these means. Through repeated doses, these drugs often cycle through concentration peaks and valleys, resulting in time periods of toxicity and ineffectiveness.

Localized drug delivery is another example. There were many different attempts to provide localized drug delivery. One example of localized drug delivery is to provide the metallic walls or wires of the stents with therapeutic substances, fibrin and other drugs that can be released over a period of time at the diseased location of the vessel. However, the incorporation of drug into the walls or wires of the stent may significantly compromise the strength of the stent.

A second example of localized drug delivery is to incorporate a drug into a stent that is constructed not of metal but of a biodegradable polymer. However, the loading in and releasing of drugs from a polymeric stent may change the structural integrity and mechanical properties of the stent.

A third example of localized drug delivery is to directly coat the metal stent with a polymer that is bonded to or contains the desired drugs or anti-stenotic substances. Unfortunately, such polymer-coated stents have not been completely effective in preventing restenosis because of the cracking of the polymer as the stent is being expanded during deployment, saturation of the drug binding sites on the stent, and other reasons.

In addition to the problems of stenosis and restenosis, the development of cancerous blockages inside body passageways (e.g., esophagus, bile ducts, trachea, intestine, vasculature and urethra, among others) can also be treated with stents, which operate to hold open passageways which have been blocked by the cancerous growth or tumors. However, the stents do not prevent the ingrowth of the cancerous material through the interstices of the stent. If the ingrowth reaches the inside of the stent, it might result in blockage of the body passageway in which the stent had been implanted.

In addition to the above-described problems experienced by localized drug delivery, conventional stents are also ineffective in preventing the ingrowth of host tissue proliferation or inflammatory material through the interstices of the stent.

Thus, there still remains a need for a prosthesis that provides effective localized drug delivery to minimize or prevent restenosis and the ingrowth of host tissue proliferation or inflammatory material through the interstices of the stent, while avoiding the disadvantages set forth above.

SUMMARY OF THE DISCLOSURE

It is an object of the present invention to provide an intraluminal prosthesis that minimizes or prevents the ingrowth of host tissue proliferation or inflammatory material through the interstices or ends of a stent.

It is another object of the present invention to provide an intraluminal prosthesis that provides effective localized drug delivery.

In order to accomplish the objects of the present invention, there is provided a prosthesis having a cylindrical stent, and a cover provided about the outer periphery of the stent. The cover has at least two layers of materials, with at least one layer of material being permeable to drugs. In one embodiment of the present invention, the layers of material define at least one chamber therebetween, and a drug is loaded into the at least one chamber. In another embodiment of the present invention, the drug can be loaded into the material of one or more layers.

BRIEF DESCRIPTION OF THE DRAWINGS

FIG. 1 is a schematic view of an intraluminal prosthesis according to one embodiment of the present invention.

FIG. 2 is a cross-sectional view of the prosthesis of FIG. 1.

FIG. 3 is a schematic view of an intraluminal prosthesis according to another embodiment of the present invention.

FIG. 4 is a cross-sectional view of the prosthesis of FIG. 3.

FIG. 5 is a schematic view of an intraluminal prosthesis according to yet another embodiment of the present invention.

FIG. 6 is a cross-sectional view of the prosthesis of FIG. 5.

DETAILED DESCRIPTION OF THE PREFERRED EMBODIMENTS

The following detailed description is of the best presently contemplated modes of carrying out the invention. This description is not to be taken in a limiting sense, but is made merely for the purpose of illustrating general principles of embodiments of the invention. The scope of the invention is best defined by the appended claims.

The present invention provides an intraluminal prosthesis that has an underlying stent with a cover acting as a sheath or sleeve. The cover acts as a drug delivery device for locally delivering a drug to a vessel wall or lumen into which the prosthesis has been inserted and positioned. The cover also functions to block the path of cell migration (i.e., ingrowth), and to pave or act as a scaffold for supporting the lumen.

The stent according to the present invention can be any stent, including a self-expanding stent, or a stent that is radially expandable by inflating a balloon or expanded by an expansion member, or a stent that is expanded by the use of radio frequency which provides heat to cause the stent to change its size. The stent can also be made of any desired material, including a metallic material, a metal alloy (e.g., nickel-titanium) or even polymeric composites. The stent can have any wire or cell design. Examples of self-expanding wire mesh stents that can be used include the coronary Wallstent™ marketed by Schneider, and the SciMED Radius™ stent marketed by Boston Scientific Corp. Examples of balloon expandable stents that can be used include the Multilink™ stent by Guidant Corp., the Coronary Stent S670 by Medtronic AVE, the Nir™ stent by Boston Scientific Corp., the Cross Flex™ stent by Cordis, the PAS™ stent by Progressive Angioplasty Systems Inc., the V-Flex Plus™ stent by Cook, Inc., and the Palmaz-Schatz™ Crown and Spiral stents by Cordis, among others. The vessels in which the stent of the present invention can be deployed include but are not limited to natural body vessels such as ducts, arteries, trachea, veins, intestines, bile ducts, ureters and the esophagus.

The term "drug" as used herein is intended to mean any compound which has a desired pharmacologic effect. Naturally, the drug is compatible with the tissue and can be tolerated in a patient. For example, the drug can be an anticoagulant, such as an RGD peptide-containing compound, heparin, antithrombin compounds, platelet receptor antagonists, anti-thrombin antibodies, anti-platelet receptor antibodies, aspirin, protaglandin inhibitors, platelet inhibitors, or tick anti-platelet peptide. The drug can also be a promoter of vascular cell growth, such as a growth factor receptor antagonists, transcriptional activator or translational promoter. Alternatively, the drug can be an inhibitor of vascular cell growth, such as a growth factor inhibitor, growth factor receptor antagonists, transcriptional repressor or translational repressor, antisense DNA, antisense RNA, replication inhibitor, inhibitory antibodies, antibodies directed against growth factors, and bifunctional molecules. The drug can also be a cholesterol-lowering agent, a vasodilating agent, and agents which interfere with endogenous vasoactive mechanisms. Other examples of drugs can include anti-inflammatory agents, anti-platelet or fibrinolytic agents, anti-neoplastic agents, anti-allergic agents, anti-rejection agents, anti-microbial or anti-bacterial or anti-viral agents, hormones, vasoactive substances, anti-invasive factors, anti-cancer drugs, antibodies and lymphokines, anti-angiogenic agents, radioactive agents and gene therapy drugs, among others. The drug may be loaded as in its/their original commercial form, or together with polymer or protein carriers, to achieve delayed and consistent release.

Specific non-limiting examples of some drugs that fall under the above categories include paclitaxel, docetaxel and derivatives, epothilones, nitric oxide release agents, heparin, aspirin, coumadin, PPACK, hirudin, polypeptide from angiostatin and endostatin, methotrexate, 5-fluorouracil, estradiol, P-selectin Glycoprotein ligand-1 chimera, abciximab, exochelin, eleutherobin and sarcodictyin, fludarabine, sirolimus, tranilast, VEGF, transforming growth factor (TGF)-beta, Insulin-like growth factor (IGF), platelet derived growth factor (PDGF), fibroblast growth factor (FGF), RGD peptide, beta or gamma ray emitter (radioactive) agents.

The cover can be made from either a tissue, a hydrogel, or a polymer, as these terms are defined hereinbelow. The tissues and hydrogels according to the present invention should have a high water content and be able to absorb fluids (i.e., liquid drugs, or drugs carried in fluids).

The term "tissue" as used herein is intended to mean any mammalian (human or animal) tissue that has sufficient strength and elasticity to act as the primary component of the prosthesis. Tissue can have a cellular matrix of proteins (e.g., collagen). Tissue can include tissue that is obtained from the host patient in which the prosthesis is to be implanted (known as autologous tissue). Tissue can also include homologous tissue, such as from cadavers, umbilical cords, and placenta. In addition, tissue can include heterologous tissue, such as from swine, canine, sheep, horse, etc. Tissue can also include tissue produced in vitro using cell culture methods. In one embodiment of the present invention, luminal tissues (e.g., venous tissue such as saphenous veins, antecubital vein, cephalic vein, omental vein, mesentric vein) are preferred. The tissue can be chemically cross-linked (e.g., by glutaraldehyde, polyepoxy, PEG, UV, etc.) or not chemically cross-linked (e.g., fresh, frozen or cryopreserved). The tissue can also be chemically modified with proper charge and hydrophilicity. The tissue can be harvested according to known techniques, such as those described in Love, *Autologous Tissue Heart Valves*, R. G. Landes Co., Austin, Tx., 1993, Chapter 8.

The term "hydrogel" as used herein is intended to mean a natural gel-like material. Hydrogel can have a polymeric matrix of proteins or polymers. Depending on the material selected, the hydrogel material may have a proper hydrophilicity to regulate the water and drug diffusion process. Hydrogel can be synthetic polymer, such as polymalic acid, polyamino acids, polyacrylic acids, polyethylene glycol, polyvinylpyrrolidone, polyvinyl alcohols, and hydrophilic polyurethanes. Hydrogel can include albumin, collagen, gelatin, starch, celluloses, dextran, polymalic acid, polyamino acids and their co-polymers or lightly cross-linked forms. Other possible materials are polysaccharides and their derivatives. Yet other possible materials include sodium alginate, karaya gum, gelatin, guar gum, agar, algin, carrageenans, pectin, locust bean gums, xanthan, starch-based gums, hydroxyalkyl and ethyl ethers of cellulose, sodium carboxymethylcellulose. Some are food gels and some are bioadhesives.

The term "polymer" as used herein means any polymeric material, such as polyurethanes, expanded PTFE, PTFE, polyesters, polyamides, polylactide, polylactide-co-glycolide, polydioxanone, thermoplastic elastomers, thermoplastics, and silicone rubbers.

The term "material" as used herein means either tissue, hydrogel, or polymer.

FIGS. 1 and 2 illustrate a prosthesis 100 according to one embodiment of the present invention. The prosthesis 100 has a tubular stent 102 and a cover 104 attached over the outer periphery of the stent 102. As described above, the stent 102 can be any known or conventional stent, and as a non-limiting example, FIG. 1 illustrates the stent 102 as being a self-expanding Nir™ stent by Boston Scientific Corp., as described in FIG. 8 of U.S. Pat. No. 5,733,303 to Israel et al., whose disclosure is incorporated herein as though fully set forth herein.

The cover 104 acts as a drug reservoir that stores the drug(s) to be released at the site of implantation of the prosthesis 100. The cover 104 is extensible (i.e., can be stretched) and flexible. The cover 104 defines a chamber or reservoir 106 that holds the drug(s) to be released. In the embodiment shown in FIGS. 1 and 2, the cover 104 has two physically separate layers of material 108 and 110 that define the chamber 106 therebetween. The cover 104 is formed by sealing the edges (e.g., by bioadhesive or suturing) of the two layers 108 and 110 to form the chamber 106. Alternatively, the layers 108 and 110 can be sequentially mounted over the stent 102. Each layer 106 and 108 can be either a tissue, hydrogel, or polymer, as defined hereinabove. In addition, the separate layers 108 and 110 can be made of the same or different materials.

At least one of the layers 108, 110 should be a drug permeable layer to allow the drug(s) stored in the chamber 106 to be released. Tissue and hydrogel are generally water permeable, and polymer can be porous or non-porous. Water and molecules can diffuse through the permeable layers 108 and/or 110 at different rates. The diffusion rate can be controlled by varying the thickness of the layer, changing the size of the migrating molecules (either the drug alone or with a carrier to form a larger molecule to slow down the diffusion process), changing the hydrophilicity of the layer, changing the drug concentration (i.e., drug released from its polymeric carrier), and coating the surface of the layer with a polymeric material having different permeability. The separate layers 108, 110 can also have different drug permeabilities. By varying the drug permeability of the layers 108, 110, a desired drug release rate can be achieved. For example, a high drug permeability for inner layer 108 will deliver most of the drug to the stent 102 and internal passageway instead of the vessel wall.

The cover 104 can be attached to the stent 102 by suturing the ends 103 of the cover 104 to the desired portions of the stent 102. For example, the cover 104 can be the same length as the stent 102, in which the ends 103 of the cover 104 are sutured (e.g., see suture 105 in FIG. 1) to the ends 120, 122 of the stent 102. If the length of the cover 104 is less than the length of the stent 102, then the ends 103 of the cover 104 can be sutured to selected wires of the stent 102 so that the cover 104 covers a portion of the stent 102. Other methods of attachment include the use of hooks or barbed mechanisms on the stent 102 to hook the cover 104 to the stent 102, or the use of glue to attach selected portions of the cover 104 to selected portions of the stent 102.

The cover 104 can be provided in the form of a tubular cover (i.e., luminal) or as a double-sheet that can be formed into a tubular cover by suturing or stitching side edges of the double-sheet. If the cover 104 is luminal, the cover 104 can be slid over the stent 102 and then attached. If the cover 104 is provided in the form of two attached sheets of material, the two sheets of material can be wrapped around the stent 102, and then attached. In either case, the attachment can be done with the stent 102 in the expanded state or in the compressed state. If the attachment is done in the expanded state, the prosthesis 100 is then compressed to a smaller diameter for delivery. When the prosthesis 100 is compressed, the flexible and stretchable nature of the cover 104 would allow the cover 104 to compress with the stent 102 without any creasing. Similarly, if the attachment is done in the compressed state, the flexible and stretchable nature of the cover 104 would allow the cover 104 to expand (e.g., stretch) with the expanding stent 102 when the prosthesis 100 is expanded.

The drug may be loaded into the cover 104 by injecting the drug (using a syringe) into the chamber 106 via the outer layer 110. Alternatively, the drug may be pre-loaded during fabrication. For example, if the cover 104 is made by mounting layers 108 and 110 sequentially over the stent 102, then after the inner layer 108 is mounted over the stent 102, the drug can be coated on to the surface of the inner layer 108 facing the chamber 108 (or the surface of the outer layer 110 facing the chamber 108) before the outer layer 110 is attached to the inner layer 108.

One or both layers 108, 110 can even be provided with perforations 118 to promote faster drug release by bypassing the normal drug diffusion process to provide a burst of drug concentration at a localized region. The number of perforations 118 provided can be varied depending on the desired burst of concentration. For example, the ends 120, 122 of the stent 102 may benefit from an initial higher dosage of drug. When the prosthesis 100 is in its collapsed state during delivery, the perforations 118 are closed (because of the flexible nature of the material for the cover 104), but are opened when the prosthesis 100 and its cover 104 are expanded.

The prosthesis 100 can be implanted using any known methods for the underlying stent 102. A catheter can be used to deliver the prosthesis 100 to the desired location in the vessel, and then the stent 102 can be expanded (i.e., either self-expanding or balloon expanded, depending on the type of stent). In essence, the prosthesis 100 will be deployed and used in the same manner as its underlying stent 102. The deployment techniques and functions of the stent 102 are well-known, and shall not be explained in greater detail.

The drug contained in the cover 104 can be released by diffusion, or by any of the methods described above.

Under certain circumstances, each material layer 108, 110 can be coated with an additional layer of tissue, hydrogel or polymer, depending on the surrounding parameters and desired application. For example, if a layer 108 or 110 is provided with a material that does not meet a desired parameter or requirement (e.g., porosity, structural strength, compatibility), an additional layer of tissue, hydrogel or polymer that does meet the desired parameter or requirement can be coated on to the layer 108 or 110 by (a) dipping the layer 108 or 110 into a solution of the coating (solution of tissue, polymer or hydrogel), (b) spraying the coating on to the layer 108 or 110, or (c) wiping the coating on to the layer 108 or 110.

In addition, the cover 104 can be comprised of more than two layers of materials. FIG. 3 illustrates a prosthesis 200 according to another embodiment of the present invention where the tubular stent 202 has a cover 204 attached over the outer periphery of the stent 202, with the cover 204 made up of three or more layers 208, 210, 212 of material to define two or more chambers 206 and 216. Each chamber 206 and 216 can be used to store the same or different drugs for delivery to different locations, as explained below. The stent 202 can be the same as stent 102, and the attachment methods described above can also be used to attach the cover 204 to the stent 202.

The inner layer 208 can function to allow drug diffusion therethrough to the stent 202 and internal passageway. The middle layer 210 can be used to separate the two drug chambers 206, 216, and if so used, should be impermeable to drugs and fluid. The outer layer 212 can function to allow drug diffusion therethrough to the diseased vessel wall. Similarly, the inner chamber 206 can be used to store drugs intended for delivery to the stent 202 and internal passageway, and the outer chamber 216 can be used to store drugs intended for delivery to the diseased vessel wall.

FIGS. 5 and 6 illustrate a further modification to the cover 104, in which the drug(s) are actually loaded on to at least one of the two layers 108 and 110 so that a chamber 106 is not needed. Each layer 108, 110 can be made from either tissue, hydrogel or polymer, and each layer 108, 110 can be loaded with different drugs or the same drugs with different dosages. The provision of the two or more drug-loaded layers 108, 110 provides better control for drug release, and allows two or more drugs to be delivered at the same time, or at the same time in different directions, and at different times. There are a number of ways of loading the drug(s) to the layers 108, 110 in the cover 104. The material utilized for the layers 108, 110 may have water content greater than 90% by weight. If so, the water can be removed by a lyophilization process that is a well-known technique in the art.

One method involves physical absorption into the layers 108, 110. Under this method, the drug is loaded into the material during the rehydration process. The drug may be dissolved in a physiological solution for rehydration of the lyophilized material. If the drug has limited solubility in water, additional solvent may be added to facilitate the dissolving process, as long as the solvent has no adverse effects on the cover and the host patient. As an example, ethanol at a concentration of less than 50% v/v may be suitable for the rehydration process. The rehydration process for tissue and hydrogel is fast, easy and complete. The material has no noticeable change in property before dehydration and after complete rehydration. By changing the hydrophilicity of the material, the drug may be released at different rates.

A second method involves the use of a charged chemical to electronically attract and retain drugs. In particular, natural tissue and certain hydrogels are proteins, which are composed of amino acids with various kinds of functional groups. By choosing the appropriate modification reagent, it is possible to selectively reduce certain groups to imbalance the surface and matrix charge of the tissue or hydrogel to either positive or negative. For example, aldehyde group will react with amino group to change the surface and matrix charge to negative. Carbodiimide reaction will target the free carboxyl group to change the surface and matrix charge to positive. Addition of charged chemicals into tissue may also change the net electricity of the tissue. A charged tissue or hydrogel material has the tendency to electronically attract and retain a drug carrying the opposite charge. The drug will then be released inside the vessel after implantation. The release of the drugs is accomplished by other charged particles in the patient's body which competes with the charged binding site in the hydrogel material for the drug.

A third method involves chemical reaction or bonding to link certain drugs to the material. The bonding may be covalent or ionic. For example, heparin may be immobilized to tissue surface covalently through direct Carbodiimide reaction or with polyethylene oxide as a bridge or spacer. Heparin can also link to tissue through ionic interaction through benzalkonium or stearylkonium. The drug may be released or remain on the surface of the tissue or hydrogel with activity in the vessel.

A fourth method involves coating the surface of the tissue or hydrogel. For example, the drug can be sprayed onto the surface, and then a gel-like material may be used to coat the tissue or hydrogel. As another example, it is also possible to first mix the gel with the drug, and then coat the mixture on to the material. As yet another example, the gel may be applied over the outer layer of the tissue or hydrogel before the drug is loaded. Then, just before implantation, the layer 108 or 110 can be immersed in a solution containing the drug, and the nature of the gel will cause the drug to be retained or loaded in the gel. The prosthesis 100 can then be delivered inside the desired vessel and the drug will be released over a period of time. Examples of the gel-like material can include polyethylene oxide, polyvinyl pyrrolidone, polyacrylates, and their blends or co-polymers or lightly crosslinked forms. Other examples include polyethylene glycol block copolymers with polylactides or other polyesters. Yet other examples include hydrophilic polyurethane, poly(maleic andydride-alt-ethylene) and their derivatives. Further examples include polysaccharides and their derivatives, sodium alginate, karaya gum, gelatin, guar gum, agar, algin, carrageenans, pectin, locust bean gums, xanthan, starch-based gums, hydroxyalkyl and ethyl ethers of cellulose, sodium carboxymethylcellulose. Some of these gel-like materials can be heated and then cooled to form the gel. Some are food gels and some are bioadhesives.

Thus, the covers 104, 204 of the present invention provide a sheath or sleeve to block the path of cell migration (i.e., ingrowth), and to pave or act as a scaffold for supporting the lumen. The covers 104, 204 act as effective drug delivery devices for locally delivering a drug to an arterial wall or lumen into which the prosthesis 100 has been inserted and positioned. The covers 104, 204 also provide, in some embodiments, a chamber 106 that can store and slowly release the desired drug in a controlled manner.

EXAMPLE 1

The cover 104 is formed of two layers of material. 1 mg of Eleutherobin is loaded into the chamber 106, and the material of the two layers 108 and 110 are then lyophilized. Because of higher incidence of problems at the two ends 120, 122 of the stent 102, more rapid drug release at the ends 120, 122 is desired. Six 2 micron holes are created at each end 120, 122 on the outer layer 110, so that each hole opens to 10 microns upon rehydration and deployment. These holes facilitate faster release of the drug.

EXAMPLE 2

Flexible polyurethane forms the outer layer 110 and porous polyurethane forms the inner layer 108 of the cover 104. The edges of the two layers 108, 110 are sealed, and heparin (low molecular weight heparin loaded at 100 unit/cover) is loaded. Heparin is only released to the internal passageway.

EXAMPLE 3

Expandable PTFE forms the outer layer 110, which is sealed with polyurethane. This outer layer 110 is not drug permeable. The inner layer 108 is made of a porous ePTFE. The two layers 108, 110 are sealed at high temperature. 5 ug of Antithrombin D-Phe-Pro-Arg Chloromethy ketone (PPACK) are loaded to the chamber 106. The drug is gradually released to the internal passageway.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A prosthesis, comprising:
a cylindrical stent having an outer periphery; and
a cover provided about the outer periphery of the stent, the cover comprising at least two layers of materials, with at least one layer of material being permeable to drugs;
wherein the two layers of material are stitched to the stent.

2. The prosthesis of claim 1, wherein the at least two layers of materials defines at least one chamber therebetween.

3. The prosthesis of claim 2, wherein a drug is loaded into the at least one chamber.

4. The prosthesis of claim 1, wherein one of the layers is made from a water absorbent material.

5. The prosthesis of claim 1, wherein one of the layers is made from a matrix of protein.

6. The prosthesis of claim 1, wherein the material of one of the layers is tissue.

7. The prosthesis of claim 1, wherein the material of one of the layers is hydrogel.

8. The prosthesis of claim 1, wherein the material of one of the layers is polymeric.

9. The prosthesis of claim 1, wherein one of the layers has at least one perforation.

10. The prosthesis of claim 1, wherein one of the layers is not impermeable to drugs.

11. The prosthesis of claim 1, wherein one of the at least two layers of materials is coated with another layer of material.

12. The prosthesis of claim 1, wherein one of the at least two layers of materials is loaded with a drug.

13. A prosthesis, comprising:
a cylindrical stent having an outer periphery;
a cover provided about the outer periphery of the stent, the cover comprising at least two layers of materials, with at least one layer of material being permeable to drugs; and
wherein the at least two layers comprises three separate layers of material that define two separate chambers.

14. The prosthesis of claim 13, wherein the three separate layers includes a non-drug-permeable middle layer that separates the two chambers.

15. The prosthesis of claim 13, wherein a drug is loaded into at least one of the chambers.

16. The prosthesis of claim 13, wherein one of the layers is made from a water absorbent material.

17. The prosthesis of claim 13, wherein one of the layers is made from a matrix of protein.

18. The prosthesis of claim 13, wherein the material of one of the layers is tissue.

19. The prosthesis of claim 13, wherein the material of one of the layers is hydrogel.

20. The prosthesis of claim 13, wherein the material of one of the layers is polymeric.

21. The prosthesis of claim 12, wherein the layers of material are stitched to the stent.

22. The prosthesis of claim 12, wherein one of the layers has at least one perforation.

23. The prosthesis of claim 12, wherein one of the layers is not impermeable to drugs.

24. The prosthesis of claim 12, wherein one of the layers of materials is coated with another layer of material.

25. The prosthesis of claim 13, wherein one of the layers of materials is loaded with a drug.

26. A cover for use in surrounding an outer periphery of a stent, comprising at least two layers of materials, with at least one layer of material being permeable to drugs; and
wherein the at least two layers comprises three separate layers of material that define two separate chambers.

27. The cover of claim 26, wherein the at least two layers of materials defines at least one chamber therebetween.

28. The cover of claim 27, wherein a drug is loaded into the at least one chamber.

29. The cover of claim 26, wherein one of the layers is made from a water absorbent material.

30. The cover of claim 26, wherein one of the layers is made from a matrix of protein.

31. The cover of claim 26, wherein the material of one of the layers is tissue.

32. The cover of claim 26, wherein the material of one of the layers is hydrogel.

33. The cover of claim 26, wherein the material of one of the layers is polymeric.

34. The cover of claim 26, wherein one of the layers has at least one perforation.

35. The cover of claim 26, wherein one of the layers is not impermeable to drugs.

36. The cover of claim 26, wherein the three separate layers includes a non-drug-permeable middle layer that separates the two chambers.

37. The cover of claim 26, wherein one of the at least two layers of materials is coated with another layer of material.

38. The cover of claim 26, wherein one of the at least two layers of materials is loaded with a drug.

39. A method of delivering drugs to the lumen of a body vessel, comprising:
providing a prosthesis having a cylindrical stent having an outer periphery, and a cover provided about the outer periphery of the stent, the cover comprising at least two layers of materials, with at least one layer of material being permeable to drugs;
loading the cover with a releasable drug;
defining a first chamber in the cover and loading the drug in the first chamber;
defining a second chamber in the cover and loading a second drug into the second chamber;
delivering the prosthesis intraluminally to a desired location in a body vessel; and releasing the drug from the cover.

* * * * *